US007125560B2

(12) United States Patent
Thakur et al.

(10) Patent No.: US 7,125,560 B2
(45) Date of Patent: Oct. 24, 2006

(54) PHARMACEUTICAL COMPOSITION OF TOPIRAMATE

(75) Inventors: Madhav S. Thakur, North Wales, PA (US); Pramod M. Kotwal, Blue Bell, PA (US); Irwin S. Gibbs, Huntington Valley, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/748,764

(22) Filed: Dec. 30, 2003

(65) Prior Publication Data

US 2004/0156901 A1 Aug. 12, 2004

Related U.S. Application Data

(62) Division of application No. 09/259,718, filed on Mar. 1, 1999, now Pat. No. 6,696,091.

(60) Provisional application No. 60/076,770, filed on Mar. 4, 1998.

(51) Int. Cl.
A61K 9/28 (2006.01)
(52) U.S. Cl. .................... 424/441; 424/492
(58) Field of Classification Search ............ 424/493, 424/494, 497
See application file for complete search history.

(56) References Cited

U.S. PATENT DOCUMENTS

| | | |
|---|---|---|
| 4,079,125 A | 3/1978 | Sipos |
| 4,205,060 A | 5/1980 | Monsimer et al. |
| 4,513,006 A | 4/1985 | Maryanoff et al. |
| 4,568,559 A | 2/1986 | Nuwayser et al. |
| 4,639,370 A | 1/1987 | Carli |
| 4,800,087 A | 1/1989 | Mehta |
| 4,851,226 A | 7/1989 | Julian et al. |
| 4,882,169 A | 11/1989 | Ventouras |
| 4,888,177 A | 12/1989 | Gergely et al. |
| 4,892,740 A | 1/1990 | Takasima et al. |
| 4,916,161 A | 4/1990 | Patell |
| 4,985,252 A | 1/1991 | Jung et al. |
| 4,994,260 A | 2/1991 | Kallstrand et al. |
| 4,994,496 A | 2/1991 | Repasky et al. |
| 5,008,117 A | 4/1991 | Calanchi et al. |
| 5,013,716 A | 5/1991 | Cherukuri et al. |
| 5,082,669 A | 1/1992 | Shirai et al. |
| 5,084,278 A * | 1/1992 | Mehta .................. 424/441 |
| 5,133,974 A | 7/1992 | Paradissis et al. |
| 5,147,655 A | 9/1992 | Ibsen |
| 5,206,030 A | 4/1993 | Wheatley et al. |
| 5,215,755 A | 6/1993 | Roche et al. |
| 5,260,072 A | 11/1993 | Roche et al. |
| 5,275,823 A | 1/1994 | Frace et al. |
| 5,286,489 A | 2/1994 | Tsau et al. |
| 5,354,566 A | 10/1994 | Addesso et al. |
| 5,393,333 A | 2/1995 | Trouve |
| 5,401,502 A | 3/1995 | Wunderlich et al. |
| 5,405,616 A | 4/1995 | Wunderlich et al. |
| 5,409,711 A | 4/1995 | Mapelli et al. |
| 5,417,985 A | 5/1995 | Coutel et al. |
| 5,425,742 A | 6/1995 | Jay |
| 5,460,825 A | 10/1995 | Roche et al. |
| 5,489,436 A | 2/1996 | Hoy et al. |
| RE35,200 E | 4/1996 | Lehmann et al. |
| 5,560,913 A | 10/1996 | Kupper et al. |
| 5,578,316 A | 11/1996 | Bhardwaj et al. |
| 5,607,697 A | 3/1997 | Alkire et al. |
| 5,633,015 A | 5/1997 | Gilis et al. |
| 5,641,513 A | 6/1997 | Lech et al. |
| 5,648,096 A | 7/1997 | Gander et al. |
| 5,705,183 A | 1/1998 | Phillips et al. |
| 5,760,007 A | 6/1998 | Shant et al. |
| 5,795,909 A | 8/1998 | Shashova et al. |

FOREIGN PATENT DOCUMENTS

| | | |
|---|---|---|
| DE | 3012136 C2 | 10/1981 |
| DE | 3943242 A1 | 6/1990 |
| DE | 4201179 A1 | 7/1993 |
| EP | 138441 B | 4/1985 |
| EP | 0287 488 B1 | 10/1988 |
| EP | 0350701 A2 | 1/1990 |
| EP | 0446753 B1 | 9/1991 |
| EP | 0317274 B1 | 3/1993 |
| EP | 0459695 B1 | 3/1995 |
| GB | 2025227 B | 1/1980 |
| GB | 2153676 | 8/1985 |
| GB | 2153677 B | 8/1985 |
| WO | 88/03795 A1 | 6/1988 |
| WO | WO 88/03795 A1 | 6/1999 |

OTHER PUBLICATIONS

D.R. Doose et al—50th Annual meeting of the American Epilepsy society, san Francisco, 1996.
The Physician's desk Reference (52nd Ed., Medical Economics Company) p. 2058.
Taber's Cyclopedia Medical Dictionary (17th Ed., F.A Davis Co.) pp. 532-534.
Janssen_Cilag Farmaceutica, LDA, "Topamax (summary of Product Characteristics of Topiramate, approved by the Portuguese Health Authorities)", 20 ABR. 2004, Comunica No. 19, p. 11-12.

(Continued)

*Primary Examiner*—Jyothsna Venkat
(74) *Attorney, Agent, or Firm*—Mary Appollina

(57) ABSTRACT

The invention is directed to a pharmaceutical composition of topiramate, an anticonvulsant which is useful for treating epilepsy. More specifically, the present invention provides a solid dosage formulation of topiramate intended primarily for use by pediatric patients, or for patients who have difficulty swallowing tablets. Processes for preparing the pharmaceutical composition are also described.

5 Claims, No Drawings

OTHER PUBLICATIONS

European Commission, Directorate General III—Industry Pharmaceuticals and Cosmetics, "Guidelines—Medicinal Products for Human Use, Quality and Biotechnology", The Rules Governing Medicinal Product in European Union, vol. 3A, pp. 143-151, 1998.

European Commission, Directorate General III—Industry Pharmaceuticals and Cosmetics, "Guidelines—Medicinal Products for Human Use, Quality and Biotechnology", The Rules Governing Medicinal Product in European Union, vol. 3A, pp. 127-141, 1998.

Simposium Terapeutico, Enciclopedia de Especialidades Farmaceuticas Portuguesas "Monography of TOPAMAX", pp. 1015-1055, 2001.

Simposium Terapeutico, Enciclopedia de Especialidades Farmaceuticas Portuguesas, "Monography of TOPAMAX", pp. 1015-1017, 2002.

Simposium Terapeutico, Enciclopedia de Especialidades Farmaceuticas Portuguesas, "Monography of TOPAMAX", pp. 974-977, 2003.

Simposium Terapeutico, Enciclopedia de Especialidades Farmaceuticas Portuguesas, "Monography of TOPAMAX", pp. 986-989, 2004.

* cited by examiner

US 7,125,560 B2

PHARMACEUTICAL COMPOSITION OF TOPIRAMATE

CROSS-REFERENCE TO RELATED APPLICATION

This application is a divisional of U.S. application Ser. No. 09/259,718, filed Mar. 1, 1999, now U.S. Pat. No. 6,696,091 which claims priority from U.S. provisional application Ser. No. 60/076,770, filed Mar. 4, 1998, the contents of which are hereby incorporated by reference.

FIELD OF THE INVENTION

The present invention provides a solid dosage formulation of topiramate and process for producing the solid dosage formulation. More particularly, the solid dosage formulation comprises core particles which are coated with a taste mask coating to provide coated particles which can be sprinkled onto food to ease administration to patients who have difficulty swallowing tablets or capsules, e.g., pediatric patients.

BACKGROUND OF THE INVENTION

The pharmaceutical industry employs a variety of dosage formulations for orally administering medicinal agents to patients. Typical formulations for oral administration include liquid solutions, emulsions, or suspensions, as well as solid forms such as capsules or tablets (as used herein, the term "tablet" means any shaped and compressed solid dosage form, including caplets). Since these conventional solid dosage formulations are usually intended for adults who can easily swallow large tablets whole, the often disagreeable taste of the active ingredient need not be taken into account in formulating the medicine, except for the provision of means to prevent the taste from being apparent during the short time that the medicine is in the mouth. Such means may include the provision of an appropriate coating on the tablet, the use of a capsule form (the gelatin outer shell of the capsule keeps the active ingredient inside until the capsule has been swallowed), or simply firmly compressing a tablet so that it will not begin to disintegrate during the short time that it is intended to be in the mouth.

Children, older persons, and many other persons have difficulty swallowing whole tablets and even capsules. Therefore, it is often desirable to provide the medicine either in liquid form or in a chewable solid form or an alternative solid form, e.g., small particles which can be sprinkled onto soft food and swallowed intact with the food, in addition to the tablet or capsule intended to be swallowed whole. Even where the medicine can be formulated as a liquid, it is desirable to provide a chewable solid form or an alternative solid form such as microspheres which can be sprinkled onto soft food (e.g., baby food) because it is often more convenient and easier to administer.

A major requirement of any such solid form is that it must be palatable, since an unpalatable formulation greatly increases the risk of a patient neglecting to take a medication. A further requirement of any solid dosage form is that it must be bioavailable; that is, once the formulation reaches the stomach, the individual particles should release the active ingredient rapidly and completely to ensure that substantially all of the active ingredient is absorbed. In cases where the active ingredient is particularly unpalatable and somewhat unstable, it may be difficult, if not impossible, to identify a solid form that fulfills both of these requirements (i.e., palatable and bioavailable).

A number of references are known which describe pharmaceutical compositions of unpalatable medicinal agents which are coated with a taste masking coating in order to hide the unpleasant taste. Julian et al., in U.S. Pat. No. 4,851,266, describe chewable medicament tablets made by coating granules of a medicament (especially, acetyl p-aminophenol) with a blend of cellulose acetate or cellulose acetate butyrate and polyvinyl pyrrolidone (also known as "PVP" and referred to hereinafter by its United States Pharmacopeia (USP) name as "povidone"). Mehta, in U.S. Pat. No. 5,084,278, discloses a pharmaceutical composition comprised of a pharmaceutical core of an active dose of a compound and a microencapsulating polymer which coats the pharmaceutical core and is capable of taste-masking the active compound. Bhardway, et al., in U.S. Pat. No. 5,578,316, describe medicament cores coated with methacrylate ester copolymers which mask the bitter and unpleasant taste of the medicament.

A variety of chlorosulfate and sulfamate esters of 2,3:4,5-bis-O-(1-methylethylidene)-β-D-fructopyranose, and their anticonvulsant activity in mammals, and thus their utility in treating diseases such as epilepsy and glaucoma, are described in U.S. Pat. No. 4,513,006. More specifically, the compound 2,3:4,5-bis-O-(1-methylethylidene)-β-D-fructopyranose sulfamate, hereinafter referred to as "topiramate", is presently available for marketing as a tablet product in strengths of 25, 50, 100, 200, 300 and 400 mg as adjunctive therapy for the treatment of adults with partial onset seizures (TOPAMAX® (topiramate) tablets). Topiramate can be prepared following the processes disclosed in U.S. Pat. Nos. 4,513,006 and 5,387,700, and preferably, by the process described in Examples 1 to 3 of U.S. Pat. No. 5,387,700. Difficulty in identifying a chewable solid form of topiramate has ensued due to the extremely bitter taste of topiramate and problems associated with stability of the active agent, especially upon exposure to moisture and heat which are known to cause degradation of topiramate. Degradation of topiramate is readily detected by changes in physical appearance, i.e., discoloration to brown or black, and by the formation of sulfate ions which can be readily detected by standard techniques know to those of ordinary skill in the art (e.g., HPLC).

Accordingly, it is an object of the invention to provide a stable solid formulation of topiramate for use in children and other patients who have difficulty swallowing conventional solid forms (e.g., tablets, capsules) which is both palatable and bioavailable. It is a further object of the invention to provide a palatable solid formulation of topiramate that can be sprinkled onto soft food prior to consumption (i.e., a "sprinkle formulation") and which provides immediate release of the active ingredient in the stomach.

SUMMARY OF THE INVENTION

The present invention is directed to a process for forming a pharmaceutical composition comprising:

(a) preparing core particles comprising an active agent of topiramate;

(b) drying the core particles from step (a) to form dried core particles;

(c) coating the dried core particles from step (b) with a taste masking mixture to form coated particles; and (d) drying the coated particles from step (c) to form the pharmaceutical composition wherein the amount of taste masking mixture ranges from about 7% by weight to about 15% by weight of the pharmaceutical composition, preferably, about 9 to about 13%, and most preferably, about 11% by weight of the pharmaceutical composition.

In another aspect of the invention is a pharmaceutical composition comprising:

(a) core particles containing an active agent of topiramate, wherein the core particles have an initial particle size between about 0.100 mm and 2.5 mm; and (b) a taste mask coating, wherein the taste mask coating comprises between about 7% by weight and about 15% by weight of the pharmaceutical composition, preferably, about 9 to about 13%, and most preferably, about 11% by weight of the pharmaceutical composition and wherein the coated particles of the pharmaceutical composition have a final particle size of about 0.100 mm to about 2.5 mm.

In one embodiment of the invention, the core particles comprise the active agent of topiramate and at least one excipient; preferably, the core particles comprise the active agent of topiramate, a binder and a diluent; more preferably, the core particles comprise the active agent of topiramate, a binder and sugar spheres.

In a class of the invention is a pharmaceutical composition comprising about 85 to about 93% by weight core beads, and about 7 to about 15% by weight of a coating; wherein the core beads comprise about 18 to about 21% by weight of topiramate, about 8 to about 11% by weight of povidone, and about 58 to about 61% by weight of sugar spheres; and the coating comprises about 6 to about 9% by weight of cellulose acetate, and about 2 to about 5% by weight of povidone.

In a subclass of the invention is the pharmaceutical composition comprising about 89% by weight of core beads and about 11% by weight coating, wherein the core beads comprise about 19.8% by weight topiramate, about 9.9% by weight povidone, and about 59.3% by weight sugar spheres; and the coating comprises about 7.2% by weight cellulose acetate and about 3.8% by weight povidone.

Illustrative of the invention are methods of treating convulsions and/or epilepsy in a mammal in need thereof which comprises administering to the mammal a therapeutically effective amount of any of the pharmaceutical compositions of the present invention.

Also included in the invention are methods of treating a condition selected from neuropathic pain, amyotrophic lateral sclerosis, acute ischemia, obesity, diabetes, psoriasis or bipolar disorder (including manic depression) in a mammal in need thereof which comprises administering to the mammal a therapeutically effective amount of any of the pharmaceutical compositions of the present invention.

DETAILED DESCRIPTION OF THE INVENTION

The present invention provides a solid dosage formulation of topiramate intended primarily for pediatric use, or for patients who cannot swallow tablets. More particularly, the solid dosage formulation is a sprinkle formulation comprising core particles of the active agent which is taste-masked with a second layer to obscure the extremely bitter taste of topiramate. The core particles can comprise topiramate alone, e.g., in granular or crystalline form, or topiramate and one or more excipients which are then formed into granules or beads by techniques known to one of ordinary skill in the art, e.g., roller compaction and comminution, extrusion-spheronization or other methods of forming granules or beads. The preferred solid dosage formulation of the present invention is in the form of microspheres which may be sprinkled onto soft food (e.g., baby food) and swallowed by the patient along with the food.

In a preferred embodiment, three strengths, 15, 25, and 50 mg, are obtained from a single sprinkle formulation of topiramate coated onto sugar spheres using povidone as a binder, and taste-masked with a coating of cellulose acetate and povidone to form coated beads. The strengths are differentiated by means of differing fill weights and of proportional capsule sizes. That is, to aid in delivery of the appropriate dosage to the patient, an amount of coated beads sufficient to deliver the desired dose may be encapsulated into a capsule, for example, a size 0, size 1, or size 2 gelatin capsule consisting of a white body with a natural cap. Black pharmaceutical ink can be utilized to provide product identification information on the capsules. For pediatric patients, the capsules can be opened and the contents of the capsules sprinkled onto food and ingested; however, mature patients may swallow drug product in intact capsules, if desired.

In general, the process for the preparation of the sprinkle formulation includes a step in which core particles comprising granules, beads or crystals of topiramate, alone or in combination with one or more excipients, are coated with a taste masking mixture and then dried. The term "particles" as used herein refers to free flowing substances of any shape which are larger than a powder including crystals, beads (smooth, round or spherical particles) and granules. A variety of methods known to those of ordinary skill in the art of pharmaceutical sciences may be employed to prepare the core particles comprising the active agent of topiramate. In one method, granules or large single crystals of topiramate can be utilized as the core particles and coated with the taste masking mixture. The coated material formed from the granules or crystals of topiramate may then be compressed into chewable tablets, if desired, or sprinkled onto soft food and swallowed.

In a second approach, the active agent of topiramate (in powder form) is first placed in a fluidized bed equipment and thereafter, a spray binder solution or suspension comprised of, for example, povidone, starch, sugar, syrup, HPMC among other excipients known to those of ordinary skill in the art in a pharmaceutically acceptable solvent (e.g., water, ethanol, acetone, among others) is sprayed onto the powder, formed into granules and then dried until the solvent is evaporated to provide the core particles. The drying temperature may vary over a broad range, but should not be so high as to render the active agent inactive As a slight modification of this second approach, a suspension of topiramate and a binder in a pharmaceutically acceptable solvent is sprayed onto sugar spheres in a fluidized bed equipment and dried to provide core beads.

In a third method for forming the core particles, powdered or granular active agent, and diluent or bulking agent are mixed with water or a pharmaceutically acceptable solvent (e.g., water, ethanol) to form a wet mass. The mixture is mixed, e.g., in a Hobart mixer or other suitable mixer, until a wet mass or dough is formed. The wet mass is then placed in an extruder and extruded as a long thin strand. The mixture may then be dried and suitably comminuted or may be placed in a suitable spheronizer to make a pharmaceutical core that is round followed by drying. The drying temperature may vary over a broad range, but should not be so high as to render the active agent inactive.

Still another approach for forming the core particles is by roller compaction of topiramate, either alone or in combination with one or more excipients. For example, topiramate in powdered or granular form can be mixed with excipient to provide suitable binding and lubricity, for example microcrystalline cellulose, magnesium stearate or talc among others, and then passed through a compactor to compact the mixture into a mass. The mass is then passed through a size reduction machine and reduced to a suitable particle size to provide the core particles.

As used herein, the term "topiramate" and "active agent of topiramate" are synonymous and are used interchangeably throughout the specification to refer to the compound 2,3:4,5-bis-O-(1-methylethylidene)-β-fructopyranose sulfamate which forms the active agent of the pharmaceutical compositions of the present invention. Topiramate and its use for treating epilepsy and glaucoma are described in U.S. Pat. No. 4,513,006. Topiramate can be synthesized according to the processes disclosed in U.S. Pat. Nos. 4,513,006 and 5,387,700, and preferably, according to the process of Examples 1–3 of U.S. Pat. No. 5,387,700.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The term "excipient," as used herein, refers to any inert substance which may be combined with an active agent for preparing convenient dosage forms, including, for example, diluents, binders, lubricants, disintegrants, colors, flavors and sweeteners.

Suitable diluents for use in the formulation and processes of the present invention include, but are not limited to, dicalcium phosphate, calcium sulfate, lactose,sorbitol, microcrystalline cellulose, kaolin, mannitol, sodium chloride, dry starch, powdered sugar and sugar spheres. In a preferred embodiment of the invention, sugar spheres (20–60 mesh, preferably, 20–40 mesh, most preferably, 20–24 mesh) are utilized as a diluent in the core beads. In a particularly preferred embodiment, sugar spheres NF (20/25 mesh) available from Crompton & Knowles Corporation as NU-PAREIL PG® are used.

Suitable binders for use in the instant formulation and processes include, but are not limited to synthetic gums such as hydroxypropyl methylcellulose ("HPMC"), povidone, carboxymethylcellulose, ethylcellulose and methylcellulose, starch, pregelatinized starch, gelatin, sugars (e.g., molasses) and natural gums (e.g., acacia gum, sodium alginate, panwar gum). Preferably, povidone (especially, Povidone USP) is used as the binder. In a particularly preferred embodiment, the povidone is PLASDONE® (K29/32) supplied by ISP Technologies, Inc. as a manufacturer of GAF products.

Disintegrants which can be utilized in the formulation and processes of the present invention include, but are not limited to, methylcellulose, cellulose, carboxymethylcellulose, croscarmellose sodium, magnesium aluminum silicate, povidone, starch, sodium starch glycolate, pregelatinized starch, alginic acid and guar gum. Preferably, the disintegrant is povidone. In a particularly preferred embodiment, the povidone is PLASDONE® (K29/32) supplied by ISP Technologies, Inc. as a manufacturer of GAF products.

Suitable taste masking agents which can be used in the formulation and processes include, but are not limited to, cellulose acetate, cellulose acetate butyrate, ethylcellulose, methylcellulose (including ethylcellulose and methylcellulose combinations), and a wide range of copolymers available under the tradename of Eudragits (Röhm Pharma of Darmstadt, Germany). In a preferred embodiment, the taste masking agent is cellulose acetate (Cellulose Acetate, NF).

A variety of solvents may be used as the first and second solvent in the processes for preparing the pharmaceutical composition. Suitable solvents include, but are not limited to, water, acetone, alcohols (e.g., methanol, ethanol, isopropanol), methylene chloride, ethyl acetate, methyl ethyl ketone, and mixtures thereof. In a preferred embodiment, the first solvent used for forming the core beads is water, and the second solvent used for coating the core beads with the taste masking mixture is an acetone-alcohol mixture, preferably, an acetone-ethanol mixture, more preferably, an acetone-dehydrated alcohol mixture.

In a preferred embodiment, a suspension of topiramate and a binder in a first solvent is sprayed onto sugar spheres (20–25 mesh) and dried to provide core beads. The core beads are then screened to remove fines and agglomerates. The core beads are coated again with a taste masking mixture and then dried. The taste masking mixture, which is sprayed onto the core beads, comprises a taste masking agent and a disintegrant dissolved or suspended in a second solvent, which may be the same or different from the first solvent. Coated beads are sifted to remove fines and agglomerates, prior to encapsulation.

In a particularly preferred embodiment of the process for preparing the sprinkle formulation, a suspension of topiramate in a solution of povidone in purified water is sprayed onto sugar spheres (20–25 mesh) and dried in a fluid bed processor equipped with a Wurster column. The ratio of topiramate:povidone utilized in the suspension can be 50:25, 50:30 or 50:35. Preferably, a 50:25 ratio of topiramate: povidone is used. The core beads then are screened to remove fines and agglomerates such that the core beads have a particle size between about 0.100 mm and about 2.5 mm, preferably, between about 0.5 mm and about 1.5 mm, most preferably, between about 0.710 mm and about 1.18 mm. The core beads are coated again with a taste masking mixture of cellulose acetate and povidone suspended in an acetone/alcohol mixture in a fluid bed unit equipped with a Wurster column, and dried. The ratio of cellulose acetate/ povidone in the taste masking mixture can be 60/40, 50/50, 65/35 or 55/45; preferably, a 65/35 ratio of cellulose acetate/ povidone is utilized. Coated beads are sifted to remove fines and agglomerates to provide a final particle size between about 0.100 mm and about 2.5 mm, preferably, between about 0.5 mm and about 1.5 mm, most preferably, between about 0.850 mm and about 1.18 mm. The coated beads are packaged (e.g., in capsules, sachets or other methods known to those of ordinary skill in the art) to deliver the desired amount of active ingredient to the patient.

When a particle size range is specified for the core and/or coated particles (e.g., between about 0.100 mm and about 2.5 mm), it is intended that at least 75%, preferably, 85%, and most preferably, 95% of the particles have a particle size falling within the specified range (e.g., about 0.100 mm and about 2.5 mm).

The invention will be described more specifically in terms of its preferred embodiment which is the preparation of a sprinkle formulation of topiramate. In the first step of the process, core beads are prepared by coating sugar spheres (20–25 mesh) with a suspension of topiramate and povidone in water. More particularly, the sugar spheres are placed in a fluidized bed coater and fluidized by a flow of warm air. The temperature of the air has not been found to be narrowly critical, and can vary over a wide range, however, the temperature should not be high enough to cause decomposition, sintering, or melting of the sugar spheres. When coating the sugar spheres with the topiramate/povidone suspension (preferably, a 50:25 ratio), a temperature from about 500 to 75° C. has been found to be suitable. The rate of air flow is adjusted so as to fluidize the sugar spheres. Such flow will vary depending on factors such as the specific equipment used, the size of the individual sugar spheres, the size of the charge of sugar spheres, the apparent specific gravity of the spheres, and other factors known to the worker in the arts relating to fluidized bed coating. After the sugar spheres have been fluidized, a previously prepared suspension of topiramate in a solution of povidone in water is sprayed onto the fluidized bed to provide the core beads. The air flow through the bed is continued until the amount of water remaining in the topiramate core beads has been substantially reduced. The core beads are actually dry to the touch within a very short time after the topiramate suspension has been sprayed onto the sugar spheres. However, the total drying time required to ensure that the water content has been reduced to the desired level may take much longer, depending on the temperature of the air, the size of the batch, and the like. Routine experimentation will suffice to determine the appropriate air temperatures and total times required in the fluidized bed coaters in individual cases. The core beads are sized through a sifter using 16 mesh and 25 mesh screens.

In the second step of the process, the core beads are coated with a taste masking mixture to provide the coated beads of the sprinkle formulation. More specifically, the core beads are placed in a fluidized bed coater and fluidized by a flow of warm air. The temperature of the air has not been found to be narrowly critical, and can vary over a wide range, keeping in mind the fact that the temperature should not be so high as to cause decomposition, sintering, or melting, of the topiramate core beads. When coating the topiramate core beads, a temperature of from 300 to 75° C. has been found to be suitable. The rate of air flow is adjusted so as to fluidize the core beads. Such flow will vary depending on factors such as the specific equipment used, the size of the charge of core beads, the size of the individual core beads, the apparent specific gravity of the core beads, and other factors known to the worker skilled in the arts of fluidized bed coating. After the core beads have been fluidized, a taste mask coating mixture is sprayed onto the fluidized bed. The taste mask coating mixture comprises a solution of cellulose acetate/povidone (preferably, in a 65:35 ratio) in an acetone-alcohol (preferably, acetone-dehydrated alcohol) solvent mixture. The air flow through the bed is continued until the amount of solvent remaining in the coating has been reduced to part per million levels. The coated beads are actually dried to the touch within a very short time after the coating solution has been sprayed onto the topiramate core beads. However, the total drying time required to ensure that the solvent content of the coating has been reduced to the level desired may take much longer, depending on the temperature of the air, the size of the batch and the like. Routine experimentation will suffice to determine the appropriate air temperature and total times required in the fluidized bed coaters in individual cases. The coated beads are then sized through a sifter using 16 mesh and 20 mesh screens.

A sprinkle formulation having satisfactory taste masking and bioavailability properties was obtained when the taste mask coating comprises about 7 to about 15% by weight of the final pharmaceutical composition. Preferably the taste mask coating comprises about 9% by weight to about 13% by weight, most preferably, about 11% by weight, of the pharmaceutical composition when dried.

Dissolution results in water indicative of bioavailability for the pharmaceutical composition having between 7 and 15% by weight taste mask coating are shown below in Table 1.

TABLE 1

DISSOLUTION RESULTS IN WATER

| Coating (%) | (%) Dissolved | | | | |
|---|---|---|---|---|---|
| | 10 min | 20 min | 30 min | 45 min | 60 min |
| 7 | 35.0 | 72.9 | 91.2 | 98.4 | 99.2 |
| 9 | 26.8 | 58.1 | 84.3 | 97.7 | 100.8 |
| 11 | 21.7 | 52.3 | 79.1 | 97.3 | 99.7 |
| 13 | 15.5 | 40.9 | 66.3 | 91.4 | 98.8 |
| 15 | 12.5 | 35.3 | 59.7 | 85.6 | 96.6 |

To aid in delivery of the appropriate dosage to the patient, an encapsulation machine can be utilized to encapsulate an amount of coated beads to provide 15 mg, 25 mg and 50 mg strengths of topiramate into a size 2, 1 or 0 gelatin capsule, respectively.

While the use of fluidized bed coating has been described in some detail as one preferred method for making the core beads and the coated beads, other techniques for making the core and coated beads readily known to those of ordinary skill in the art may be used. Such other techniques include various microencapsulation techniques such as coacervation and solvent evaporation.

In a particularly preferred embodiment, the ingredients and amounts of each ingredient used to prepare the topiramate sprinkle bead formulation are provided in Table 2.

TABLE 2

TARGET COMPONENT/COMPOSITION

| INGREDIENT | REFERENCE | ROLE | Unit Dosage Strength (mg) | | |
|---|---|---|---|---|---|
| | | | 50 mg | 25 mg | 15 mg |
| Topiramate | | Active | 50.0 | 25.0 | 15.0 |
| Povidone | USP | Binding Agent | 25.0 | 12.5 | 7.5 |
| Purified Water[1] | USP | Process Aide | — | — | — |
| Sugar Spheres, 20–25 mesh | NF | Core Bead | 150.0 | 75.0 | 45.0 |
| Cellulose Acetate | NF | Film Coat | 18.076 | 9.038 | 5.423 |
| Povidone | USP | Film Coat | 9.733 | 4.8665 | 2.9199 |
| Acetone[1] | NF | Process Aide | — | — | — |
| Dehydrated Alcohol[1] | USP | Process Aide | — | — | — |
| Gelatin Capsules | Type IV | Drug Product Holder | one unit (Size 0) | one unit (Size 1) | one unit (size 2) |
| Printing Ink | | Identifier | | | |

[1]Essentially removed during drying.

The strengths of topiramate sprinkle capsules, 15, 25 and 50 mg are obtained from a single formulation of topiramate-coated beads by encapsulating the proportionate amounts of coated beads in appropriately sized and marked capsules. Table 3 provides a batch formula for a production batch of topiramate sprinkle bead formulation.

TABLE 3

BATCH FORMULATION
TARGETED FORMULATION

| INGREDIENT | TARGET (kg) | RANGE(kg) | RANGE (%) |
|---|---|---|---|
| CORE BEADS | | | |
| Topiramate | 37.5 | — | — |
| Povidone, USP | 18.75 | ±0.09375 | ±0.5% |
| Purified Water, USP[1] | 93.75 | ±0.9375 | ±1.0% |
| Sugar Sphere, NF 20–25 mesh | 112.50 | — | — |
| Core Bead Batch Size | 168.75 | | |
| COATED BEADS | | | |
| Core Beads | 150.00 | | |
| Cellulose Acetate, NF | 12.051 | ±0.12051 | ±1.0% |
| Povidone, USP | 6.489 | ±0.06489 | ±1.0% |
| Acetone, NF[1] | 120.00 | ±1.2% | ±1.0% |
| Dehydrated Alcohol, USP[1] | 30.00 | ±0.3% | ±1.0% |
| Coated Bead Batch Size | 168.54 | | |
| GELATIN CAPSULES | | | |
| Gelatin | | | |
| Print Ink | | | |

[1]Essentially removed during drying.

A comparison of dissolution rates in water between TOPAMAX® 100 mg tablets and topiramate sprinkle capsule formulations, 25 and 50 mg dosages (according to the specifications of Table 2) are shown in Table 4.

TABLE 4

DISSOLUTION COMPARISON

| | % Label Dissolved (mean) | | | |
|---|---|---|---|---|
| Product | 10 min | 20 min | 30 min | 45 min |
| 100 mg Tablet | 85.0 (79–89) | 92.6 (89–96) | 96.4 (93–99) | — |
| 25 mg Sprinkle | 19.7 (17–22) | 51.4 (48–55) | 75.0 (71–80) | 94.7 (90–99) |
| 50 mg Sprinkle | 17.8 (17–19) | 48.1 (45–50) | 71.3 (69–73) | 93.5 (91–96) |

The stability of the sprinkle formulation of the present invention was compared to TOPAMAX® (topiramate) tablets by storing both formulations in controlled stability chambers for the purpose of determining the stability profile for the two products. Samples were stored at 30° C. The sprinkles were stored at 60% relative humidity (RH); relative humidity for the tablet batches was either controlled at 35% RH or was not controlled, but, in any event, was well below 60% RH. Data were collected for assay (amount of drug remaining), sulfate and sulfamate, physical appearance at selected time intervals, e.g., 18 months, 24 months. Physical appearance, i.e., discoloration to brown or black, and amount of sulfate detected are good indicators of degradation of the active agent (topiramate). For each mole of topiramate that degrades, a molar equivalent of inorganic impurity (sulfate/sulfamate) is formed. The presence of inorganic impurity is readily determined by one of ordinary skill in the art using standard techniques, e.g., HPLC.

At 18 months, some instability was detected by appearance data for the tablets, while the sprinkle formulation showed no signs of instability/degradation. Clear signs of degradation were apparent by appearance and sulfate data for the tablets at 24 months. After 24 months of storage at 30 degrees 60% RH, the 25 and 50 mg strengths of sprinkle capsules remained stable while the 15 mg strength showed instability. At 25 degrees 60% RH storage for 24 months, all three strengths of the sprinkle formulation remained stable.

It is known that moisture accelerates the degradation of topiramate. It has now been unexpectantly found that the coating used to taste mask the topiramate core beads also provides a barrier to the absorption of moisture, and therefore, improves on the stability of the sprinkle formulation. For storage of the tablets, it was necesssary to put a desiccant into the bottles to stabilize the tablet formulation. However, there is no need for a dessicant for the sprinkle formulation. In addition, the capsules which are used to ease delivery of the appropriate dosage of sprinkles contain more than 10% moisture by weight, and yet, this moisture does not accelerate the degradation of topiramate because of the taste mask coating for the sprinkles.

The following examples are provided to further define the invention without, however, limiting the invention to the particulars of these examples.

EXAMPLE 1

Preparation of Core Beads

| Ingredient | Batch Amount (kg) |
|---|---|
| Topiramate | 37.50 |
| Povidone, USP | 18.75 |
| Sugar Spheres, NF (20–24 mesh) | 112.50 |
| Purified Water, USP | 93.70 |

Batch amounts of each of the core bead ingredients were accurately weighed out. In a jacketed kettle (approximately 60 gallons) equipped with a sweeper, a homogenizer (Silverson or equivalent) and a mixer (LIGHTNIN'® or equivalent) was placed the appropriate batch amount of purified water, USP. The batch amount of Povidone, USP was added and the resulting mixture mixed for a minimum of 15 minutes to disperse the povidone in the purified water. The topiramate (37.50 kg) was added and the mixture mixed for a minimum of 15 minutes to disperse. Water was passed through the jacket. Using the mixer and homogenizer, the topiramate suspension was homogenized for approximately 90 minutes (range: 80–100 minutes). Stirring was continued through the steps which follow for preparing the core beads.

A pump (Masterflex or equivalent) was prepared with three pump heads for spraying. The batch quantity of sugar spheres, NF was charged to a fluid bed (Glatt Fluid Bed equipped with a 32 inch Wurster column, 3 guns with 2.2 mm nozzles, or equivalent). The sugar spheres were fluidized and the topiramate suspension sprayed through the nozzles (approximate spray rate: 1 kg/min; approximate spray time: 2.25 hours) according to the parameters shown in Table 5.

TABLE 5

| Operating Function | Operating Parameter |
|---|---|
| Air Flow | 2400 CFM (range: 1900–2900 CFM) |
| Inlet Air Temperature | 60° C. (range: 50° C.–70° C.) |
| Bed Temperature | 40° C. (range: 38° C.–45° C.) |
| Atomization Air | 3 bar (range: 2.7–3.5 bar) |

The core beads were dried at 60° C. for at least 15 minutes (range: 15–18 minute) after the bed temperature had reached 60° C. (range: 55° C.–65° C.) according to the parameters provided in Table 6.

TABLE 6

| Operating Function | Operating Parameter |
|---|---|
| Air Flow | 2100 CFM (range: 1800–2200 CFM) |
| Inlet Air Temperature | 60° C. (range: 50° C.–70° C.) |
| Atomization Air | 1 bar (range: 1–2 bar) |

The core beads were then sized through a 48" sifter (Sweco or equivalent), using 16 mesh and 25 mesh screens to remove fines and agglomerates.

EXAMPLE 2

Preparation of Coated Beads

| Ingredient | Batch Amount (kg) |
|---|---|
| Topiramate —Core Beads | 150.00 |
| Cellulose Acetate, NF | 12.051 |
| Povidone, USP | 6.489 |
| Acetone, NF | 120.00 |
| Dehydrated Alcohol, USP | 30.00 |

The batch quantites of Acetone, NF and Dehydrated Alcohol, USP were transferred to a suitable stainless steel tank and mixed. The batch quantity of Povidone, USP was added using a suitable mixer (LIGHTNIN'® or equivalent). The batch quantity of Cellulose Acetate, NF was added at the vortex while mixing with a suitable mixer and the coating solution was checked visually for clarity.

The 16/25 mesh topiramate core beads (150 kg) from Example 1 were fluidized in a Glatt Fluid Bed processor equipped with a Wurster column (or equivalent). The core beads were sprayed with the coating solution until the entire quantity of coating solution was exhausted. The coated beads were dried at approximately 60° C. for a minimum of 30 minutes (range: 28–32 minutes). Operating parameters are shown in Table 7.

TABLE 7

Operating Ranges for Spraying/Drying

| Parameter | Operating Range |
|---|---|
| Inlet Air Flow | 1500–3000 CFM |
| Inlet Air Temperature | 30° C.–70° C. |
| Atomization Air | 1–4 bars |
| Bed Temperature | 30° C.–70° C. |

A Sweco Sifter (or equivalent equipment) was fitted at the top with a 16 mesh screen and at the bottom with a 20 mesh screen. The entire batch of coated beads was sieved and coated beads outside the 16–20 mesh range discarded.

EXAMPLE 3

Encapsulation of Coated Beads

An encapsulation machine (H&K Encapsulator or equivalent) was prepared with a bead filler attachment and the coated beads from Example 2 encapsulated.

Target fill weights were determined by assay of the coated beads prior to encapsulation. Variability of the fill weight was controlled by weight sorting, which is required for the 15 mg strength, but optional and employed as necessary for the 25 and 50 mg strengths. A KKE sorting machine (or equivalent) was used to weigh the filled capsules when weight sorting was employed. Filled capsules not meeting the acceptable weight range were discarded by the sorter.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of treating convulsions in a mammal in need thereof which comprises administering to the mammal a therapeutically effective amount of a pharmaceutical composition comprising
   (a) core particles containing an active agent of topiramate, a binder and a diluent wherein the diluent is sugar spheres and wherein the core particles have an initial particle size between about 0.710 mm and 1.18 mm; and
   (b) a taste mask coating, wherein the taste mask coating comprises between about 9% by weight and about 13% by weight of the pharmaceutical composition and wherein the coated particles of the pharmaceutical composition have a final particle size between about 0.850 mm and 1.18 mm; and
   wherein the coated particles are sprinkled onto soft food and swallowed.

2. The method of claim 1, wherein the taste mask coating comprises about 11% by weight of the pharmaceutical composition.

3. The method of claim 1, wherein the binder is selected from povidone, HPMC, sodium alginate, panwar gum, acacia gum, gelatin, sugar, molasses, starch, pregelatinized starch, methycellulose, ethylcellulose or caroboxymethylcellulose; and the taste mask coating comprises a taste masking agent and a disintegrant, wherein the taste masking agent is selected from cellulose acetate, methylcellulose, ethylcellulose, a Eudragit or cellulose acetate butyrate; and the disintegrant is selected from povidone, cellulose, carboxymethylcellulose, croscarmellose sodium, magnesium aluminate silicate, starch, sodium starch glycolate, pregelatinized starch, alginic acid or guar gum.

4. The method of claim 3, wherein the binder is povidone, the taste masking agent is cellulose acetate and the disintegrant is povidone.

5. The method of claim 4, wherein the coated particles of the pharmaceutical composition are encapsulated.

* * * * *